United States Patent [19]

Beeby

[11] 4,049,806

[45] Sept. 20, 1977

[54] CEPHALOSPORIN TYPE ANTIBACTERIALS

[75] Inventor: Philip J. Beeby, Melbourne, Australia

[73] Assignee: Syntex (U.S.A.) Inc., Palo Alto, Calif.

[21] Appl. No.: 605,109

[22] Filed: Aug. 15, 1975

[51] Int. Cl.$^2$ ............................................. C07D 501/24
[52] U.S. Cl. ...................................... 424/246; 542/400; 542/402; 544/3; 544/16
[58] Field of Search ............ 260/240 R, 240.1, 243 C; 424/246

[56] References Cited

U.S. PATENT DOCUMENTS

| | | | |
|---|---|---|---|
| 3,660,395 | 5/1972 | Wright | 260/243 C |
| 3,769,277 | 10/1973 | Long | 260/243 C |
| 3,830,700 | 8/1974 | O'Callaghan et al. | 424/246 |
| 3,852,277 | 12/1974 | Jacobus | 424/246 |
| 3,929,780 | 12/1975 | Weir | 260/243 C |

*Primary Examiner*—Arthur P. Demers
*Attorney, Agent, or Firm*—Lawrence S. Squires; William B. Walker; Natalie Jensen

[57] ABSTRACT

3-[3-(1-Methyltetrazol-5-ylthio)-prop-1-(t)-enyl]-7β-(α-phenylacetamido)-ceph-3-em-4-carboxylic acid; 7β-(α-phenylacetamido)-3-[3-(1,2,4-triazol-5-ylthio)-prop-1-(t)-enyl]-ceph-3-em-4-carboxylic acid derivatives and salts thereof; and intermediates and processes for preparing such compounds. The compounds are useful as antibacterials and are active against a wide variety of gram positive and gram negative bacteria.

39 Claims, No Drawings

CEPHALOSPORIN TYPE ANTIBACTERIALS

BACKGROUND OF THE INVENTION

1. The Invention

This invention relates to cephalosporin type compounds, having antibiotic activity, and intermediates and processes for preparing such compounds. In a further aspect, this invention relates to 3-[3-(1-methyltetrazol-5-ylthio)-prop-1-(t)-enyl]-7β-phenylacetamido)-ceph-3-em-4-carboxylic acid; 7β-(α-phenylacetamido)-3-[3-(1,2,4-triazol-5-ylthio)-prop-1-(t)-enyl]-ceph-3-em-4-carboxylic acid; and to derivatives and salts thereof; and to intermediates for, and methods of, preparing such compounds. In a still further aspect, the invention relates to pharmaceutical compositions and antiseptic compositions containing such compounds and to methods of destroying and/or inhibiting the growth of gram negative and/or gram positive bacteria.

2. The Prior Art

Since the first discovery that certain derivatives of Cephalosporin C exhibit potent antibiotic activity, a large number of cephalosporin type compounds have been synthesized for possible improved, or different, antibiotic activity and selectively note, for example, U.S. Pat. Nos. 3,769,277, 3,830,700, 3,853,860, 3,859,274, 3,864,338 and 3,867,380. A general discussion of celphalosporins can be found in *Cephalosporins and Penicillins Chemistry and Biology*, edit E. H. Flynn, Academic Press, Inc. (1972).

SUMMARY

In summary, the compounds of the invention can be represented by the following generic formulas:

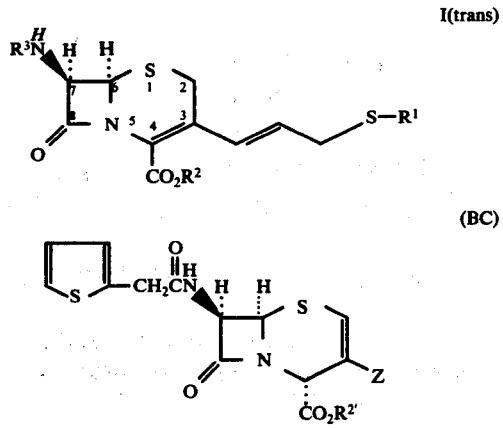

wherein
$R^1$ is 1-methyltetrazol-5-yl; or 1,2,4-triazol-5-yl;
$R^2$ is hydrogen, or a protecting group selected from the group of diphenylmethyl, benzyl, o-nitrobenzyl, p-nitrobenzyl, 3,5-dinitrobenzyl, p-metoxybenzyl, t-butyl, pivaloyloxymethyl, phenacyl, and polyhaloalkyl having two to six carbon atoms, e.g. 2,2,2-trichloroethyl; $R^3$ is hydrogen or a group having the formulas

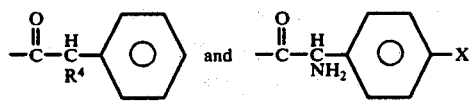

wherein
X is hydrogen, or hydroxy and $R^4$ is hydrogen, hydroxy, sulfo or carboxy;
$R^{2'}$ is a protecting group selected from the same group of protecting groups as $R^2$;
Z is a group having the formula

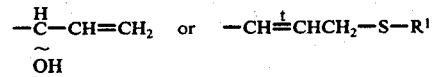

wherein the $\sim$OH indicates both the α-and β-orientation and mixtures thereof and $R^1$ is as defined above, and t indicates trans orientation.

The pharmaceutically acceptable salts of the above compounds, wherein $R^3$ is other than hydrogen, with respect to the C-4 acid and $R^4$-sulfo and carboxy moieties, are also encompassed within the scope of the invention. Also, as can be seen from formulas I and BC, the stereo configuration of the propenyl double bond is trans and the amino or carbonylamino substituent at the 7 -position is beta oriented.

In summary, one process of the invention comprises reacting a 3-formyl-7β-(thiophen-2-yl-acetamido)-ceph-2-em-4-carboxylate ester with a vinyl Grignard reagent to yield the corresponding 3-(1-hydroxyprop-2-enyl)-7β-(thiophen-2-yl-acetamido)-ceph-2-em-4-carboxylate ester intermediate of formula BC and reacting this intermediate with a mercapto-1-methyltetrazol-5-yl or 1,2,4-triazol-5-yl to yield the corresponding heterocycle-ylthioprop-1-(t)-enyl intermediate of formula (BC).

In summary, a further process of the invention comprises rearrangement of the C-2(3) double bond of the heterocycleylthioprop-1-(t)-enyl intermediate, of formula (BC) to C-3(4) and then cleaving the 7β-thiophen-2-yl-carbonyl moiety to yield the 7β-amino intermediates of formula I ($R^3$ is H).

Another process of the invention comprises acylation of the 7β-amino group of the 7β-amino intermediate of formula I and hydrolysis of the 4-carboxylate ester protecting group, or vice-versa, to yield the corresponding 4-carboxylic acid of formula I, and optional treatment with a pharmaceutically acceptable cation to yield the corresponding salts.

In summary, the pharmaceutical compositions and antiseptic composition, of the invention, comprise the 4-carboxylic acid compounds of formula I, and/or pharmaceutically acceptable salt thereof, and a pharmaceutically acceptable carrier or antiseptic carrier.

In summary, the process of the invention for reducing or inhibiting bacterial infections comprises administering an effective amount of the carboxylic acids of formula I, or a pharmaceutically acceptable salt thereof, to mammals suffering from such infections, or in the case of undesired bacterial growth on inanimate objects, applying an effective amount of the aforementioned in compounds in an antiseptic carrier to such objects.

The invention will be further described hereinbelow.

FURTHER DESCRIPTION OF THE INVENTION AND PREFERRED EMBODIMENTS

The compounds of the invention can be represented by the following sub-generic formulas:

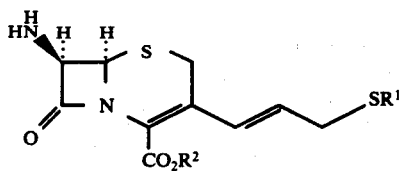

II

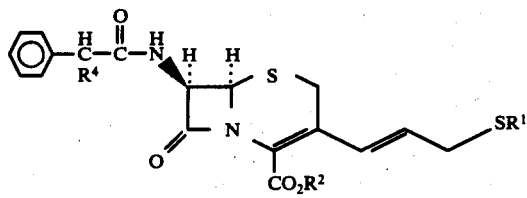

III

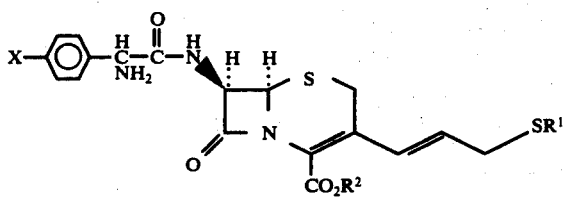

IV

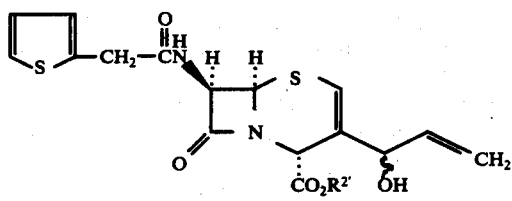

(B)

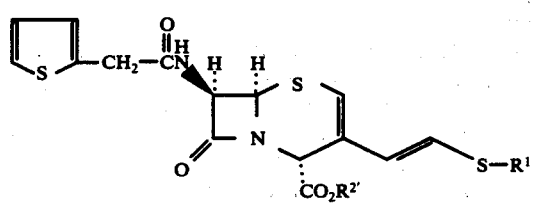

(C)

wherein $R^1$ is 1-methyltetrazol-5-yl or 1,2,4-triazol-5-yl, $R^2$ is hydrogen or a protecting group selected from the group of diphenylmethyl, benzyl, o-nitrobenzyl, p-nitrobenzyl, 3,5-dinitrobenzyl, p-methoxybenzyl, t-butyl, pivaloyloxymethyl, phenacyl, and polyhaloalkyl having two to six carbon atoms, e.g. 2,2,2-trichloroethyl;

$R^{2'}$ is a protecting group selected from the same group of protecting group as $R^2$;

$R^4$ is hydrogen, hydroxy, sulfo or carboxy;

X is hydrogen or hydroxy, and the wavy bond line $\sim$OH in formula B indicates both the $\alpha$- and $\beta$-orientation and mixtures thereof.

Also encompassed within the invention are the pharmaceutically acceptable salts of the compounds of formula III and IV.

The compounds of formula III wherein $R^4$ is hydroxy, sulfo or carboxy, and the compounds of formula IV exist as optical isomers; accordingly, the above formulas are intended to represent the respective (D) and (L) optical isomers as well as mixtures thereof and the individual isomers as well as mixtures thereof are encompassed within the invention. Generally, in terms of antibiotic activity, the (D) optical isomers are preferred.

Also, as previously noted, the C-7 position amino or carbonylamino substituent is beta oriented and the propenyl double bond is trans oriented.

Typical illustrations of the compounds of formulas B, C and II can be had by reference to Examples 1, 2, 4, and 7, respectively, set forth hereinbelow.

Typical illustrations of the compounds of formulas III and IV can be had by reference to Examples 5, 5A, 6, 6A, 8 5B, 6B, 8B, respectively, hereinbelow.

The preferred compounds of formulas III and IV, with respect to the $R^1$ substituent, are those wherein $R^1$ is 1-methyltetrazol-5-yl, the preferred $R^3$ substituents are $\alpha$-hydroxy-$\alpha$-phenylacetamido; $\alpha$-amino-$\alpha$-phenylacetamido; and $\alpha$-amino-$\alpha$-p-hydroxyphenylacetamido. The particularly preferred compounds of formulas III and IV are:

7$\beta$-D-($\alpha$-hydroxy-$\alpha$-phenylacetamido)-3-[3-(1-methyltetrazol-5-ylthio)-prop-1-(t)-enyl]-ceph-3-em-4-carboxylic acid;

7$\beta$-D-($\alpha$-amino-$\alpha$-phenylacetamido)-3-[3-(1-methyltetrazol-5-ylthio)-prop-1-(t)-enyl]-ceph-3-em-4-carboxylic acid;

7$\beta$-D-($\alpha$-amino-$\alpha$-p-hydroxyphenylacetamido)-3-[3-(1-methyltetrazol-5-ylthio)-prop-1-(t)-enyl]-ceph-3-em-4-carboxylic acid;

and pharmaceutically acceptable salts thereof.

In terms of convenience, the sodium salts are preferred correspondingly the particularly preferred salts are the sodium salts of the preferred and particularly preferred compounds of formulas III and IV. The preferred and particularly preferred compounds of formula II are the corresponding precursors of the preferred and particularly preferred compounds of formulas III and IV.

The processes of the invention for preparing the compounds of the invention can be schematically represented by the following sequence of overall reaction equations:

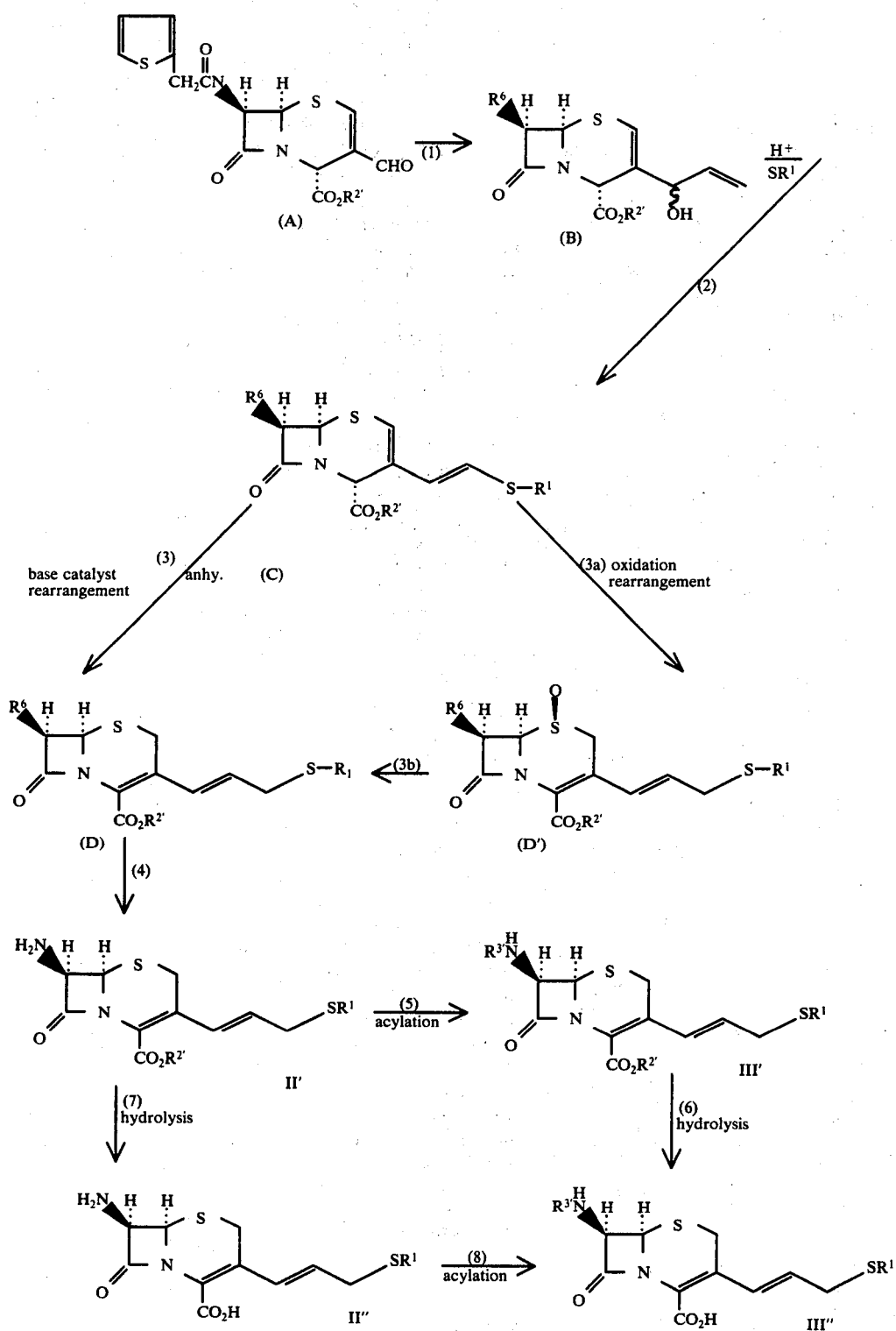
wherein
R2′ is a suitable protecting group, e.g. diphenylmethylene, R1 is as defined hereinabove, and R6 is the group
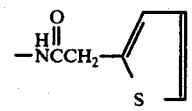
and R3′ is the group -continued

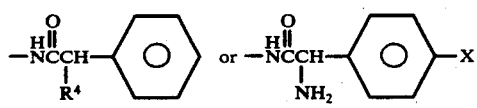

wherein R⁴ and X are as defined hereinabove, and the ~OH in formula B indicates a mixture of α- and β-hydroxy isomers.

Step 1, of the above process, can be conveniently effected by treating the starting material of formula A with a suitable vinyl Grignard reagent, preferably in a suitable inert organic solvent. Typically, this treatment is conducted at temperatures in the range of −100° to −20° C, preferably about from −60° to −80° C, for about from 0.25 to 2.0 hours, and preferably about from 0.25 to 0.5 hours. Typically, a mole ratio of Grignard reagent to compound of formula A of about from 3 to 10, preferably about from 4 to 5, is used. Typically, and preferably, the treatment is conducted under anhydrous conditions and under an inert atmosphere; e.g. nitrogen. Suitable inert organic solvents which can be used include, for example, tetrahydrofuran, dimethoxyethane, dioxane and the like, and mixtures thereof. Suitable Grignard reagents which can be used include, for example, vinyl magnesium chloride, vinyl magnesium bromide and the like. The resulting product is a mixture of α- and β-hydroxy isomers which, if desired, can be resolved by conventional procedures.

The starting materials of formula A are known compounds and can be prepared according to known procedures such as, for example, described in U.S. Pat. No. 3,864,338, and in the Preparations set forth hereinbelow; or by obvious modifications of such procedures; e.g. by substitution of protecting groups.

Step 2, of the process, can be conveniently effected by treating the compound of formula B (either the respective α- or β-hydroxy isomers or mixtures thereof) with a mercapto substituted heterocycle corresponding to the desired SR¹ substituent, in the presence of a small amount of a strong acid (e.g. typically about 0.01 to 0.1 moles per mole of the compound of formula B). Typically, this treatment is conducted at temperatures in the range of about from 0° to 50° C, preferably about from 35° to 45° C for about from two to 24 hours, preferably about from 6 to 8 hours using mole ratios of mercapto heterocycle to the compound of formula B of about from 1.0 to 5.0, preferably from 1.1 to 1.5. Suitable inert organic solvents which can be used include, for example, tetrahydrofuran, dimethoxyethane, dioxane, chloroform, methylene chloride and the like. Suitable inert strong acids which can be used include, for example, perchloric acid, hydrochloric acid, hydrobromic acid, sulfuric acid, and the like. Suitable organic acids which can be used include, for example, p-toluenesulfonic acid, trifluoroacetic acid, and the like. Typically, superior results are obtained using p-toluenesulfonic acid.

Step 3, rearrangement of the cephem double bond and the orientation of the C-4-position ester group, can be conveniently effected by treating the compound of formula C with a catalytic of triethylamine in pyridine. Typically, this treatment is conducted under anhydrous conditions at temperatures in the range of about from 0° to 40° C, preferably about from 20° to 25° C for about from 10 to 72 hours, preferably about from 24 to 36 hours using mole ratios of triethylamine to compound of formula C of about from 0.01 to 1.0, and preferably about from 0.05 to 0.1. Suitable organic solvents which can be used include, for example, pyridine, quinoline, N,N-dimethylaniline, and the like, and mixtures thereof. Also, in place of triethylamine, the following reagents could also be used, diisopropylethylamine, 1,6-diazabicyclo [5,4,0]undec-non-1-ene, 1,5-diazabicyclo [4,3,0]non-1-ene and the like. Alternatively, this rearrangement can be effected in two steps (3a and 3b) via the intermediate D'. Step 3a can be conveniently effected by treating the compound of formula C with m-chloroperbenzoic acid in a suitable inert organic solvent. Typically, this treatment is conducted at temperatures in the range of about from −10° to 25° C, preferably about from 0° to 5° C for about from 0.5 to 24 hours, preferably about from three to five hours, using mole ratios of m-chloroperbenzoic acid to compound of formula C of about from 1.0 to 1.2. Preferably this mole ratio should be close to one (about from 1.05 to 1.1) to prevent over oxidation of the thio moiety to sulfonyl). Suitable inert organic solvents which can be used include, for example, methylene chloride, chloroform, and the like, and mixtures thereof. Also, in place of m-chloroperbenzoic acid, the following reagents could also be used, perbenzoic acid, peracetic acid, hydrogen peroxide, sodium metaperiodate, ozone, and the like. Step 3b can be conveniently effected by treating the sulfo oxide of formula D' with a mixture of stannous chloride and acetyl chloride in a suitable inert organic solvent, preferably under an inert atmosphere. Typically, this treatment is conducted at temperatures in the range of about from −10° to 25° C, preferably from 0° to 5° C for about from 0.25 to 5.0 hours, preferably about from 1.0 to 2.0 hours using mole ratios of stannous chloride to compound of formula D' of about from 1.5 to 5.0, and preferably about from 2.0 to 3.0. Also, in place of stannous chloride and acetyl chloride, the following reagents could also be used, phosphorous trichloride, phosphorous tribromide, and the like, and mixtures thereof.

Step 4 of the process can be conveniently effected by treating the compound of formula D with phosphorous pentachloride in an inert organic solvent, in the presence of pyridine. This portion of step 4 is typically conducted under anhydrous conditions and under an inert atmosphere at temperatures in the range of about from 10° to 30° C for about from 2.0 to 4.0 hours using 1.1 to 1.2 moles of pyridine and about from 1.1 to 1.2 moles of phosphorous pentachloride per mole of compound of formula D. After the resulting reaction has been substantially completed, about from two to 10 moles of isobutyl alcohol, preferably about five, per mole of formula D is added to the product mixture, and the treatment continued at temperatures in the range of about from −20° to 30° C, preferably about from 0° to 5° C for about from 0.25 to 2.0 hours, preferably about from 0.5 to 1.0 hours. A small quantity of water is then added to effect the final reaction in this treatment. This final step is typically conducted at temperatures in the range of −20° to 30° C, preferably about 0° to 5° C for about from 0.1 to 1.0 hours, preferably about from 0.25 to 0.5 hours. Suitable inert organic solvents which can be used for this treatment include, for example, chloroform, and the like. Also, in place of pyridine, the following compounds could, for example, be used, quinoline, N,N-dimethylaniline, and the like. Also, in place of isobutyl alcohol, other lower alkanols could be used, for example, methanol, ethanol, and the like or mixtures thereof.

The next two steps of the process, i.e. acylation of the amino group and, if desired, removal of the ester group can be conducted interchangeably. Hence, the ester group can first be cleaved (step 7) and then the amino group acylated (Step 8), or vice versa (i.e. steps 5 and 6). Step 7 or 6 can be effected by conventional procedures used by the art to cleave ester groups to yield the corresponding free acid, for example, benzhydryl and p-methoxybenzyl can be conveniently cleaved via treatment with a trifluoroacetic acidanisole mixture (typically 2:1 to 6:1 mole ratio) at 0-5° C for about from two to five minutes in an inert solvent; e.g. methylene chloride, benzene, and the like.

Steps 5 and 8 can be effected by conventional amino acylation procedures. For example, steps 5 to 8 can be conveniently effected by treating the compound of formula II' with about from 1.1 to 1.5 stoichiometric equivalents of an acyl halide, having the desired benzylcarbonyl or substituted benzylcarbonyl acyl moiety, in an inert organic solvent (e.g. dichloromethane, chloroform, etc.) in the presence of an organic or inorganic base (e.g. sodium bicarbonate; pyridine; triethylamine and the like) at temperatures in the range of about from 0° to 5° C for about from 0.5 to one hour. Typically, about from two to 10 stoichiometric equivalents of the base is used. The acylation can also be effected via treatment with a carboxy acid, having the desired $R^3$ moiety (i.e. $R^{3'}COOH$) and a suitable coupling reagent, e.g. dicyclohexyl carbodiimide, N-ethoxycarbonyl-2-ethoxy-1,2-dihydroquinoline, in a suitable inert organic solvent, e.g. dichloromethan. In the case of groups having an α-hydroxyacetyl or an α-free amino-acetyl, it is preferred to use acyl halides, or $R^3$ acids, in which the free hydroxy or free amino group is protected with a suitable protecting group which can be easily cleaved to yield the corresponding α-hydroxy or α-amino compounds of formula III' or III". For example, the α-hydroxy compounds of formula III' or III" can be conveniently prepared via acylation with α-dichloroacetoxyphenacetyl halide to yield the corresponding o-dichloroacetyl protected free hydroxy derivative of formula III' or III". The dichloroacetyl protecting group can then be removed via mild base hydrolysis. Similarly, the α-free amino compound of formula III' and III" can be prepared via acylation with D-(—)-α-(t-butoxycarbonylamino)-α-phenylacetic acid to yield the corresponding t-butoxycarbonyl protected α-amino derivative of formulas III' and III". The t-butoxycarbonyl protecting group can then be removed via acid hydrolysis. In either case, if the C-4 carboxy protecting group is also cleaved during the acid hydrolysis, it can be selectively replaced, if desired, via conventional procedures; for example, in the case of diphenylmethyl protecting groups via treatment with about a molar equivalent amount of diphenyldiazomethane.

The optical isomers of formulas III ($R^4$ is hydroxy, carboxy or sulfo) and IV can be conveniently prepared by using the corresponding optically active acyl halide or $R^3$ acid in the acylation step (step 5 to 8)).

It is generally preferred that the respective products of each process step, described hereinabove, be separated and/or isolated prior to its use as starting material for subsequent steps. Separation and isolation can be effected by any suitable or purification procedure such as, for example, evaporation, crystallization, column chromatography, thinlayer chromatography, distillation, etc. Specific illustrations of typical separation and isolation procedures can be had by reference to the appropriate examples described hereinbelow; however other equivalent separation procedures could, of course, also be used. Also, it should be appreciated that where typical reaction conditions (e.g. temperatures, mole ratios, reaction times) have been given that conditions both above and below these ranges can also be used, though generally less conveniently.

The pharmaceutically acceptable salts, of the invention, can be prepared according to procedures which are well known in the art, for example, by simply treating the free acid of formula I with an inorganic or organic base having the desired salt cation, e.g. sodium hydroxide, potassium hydroxide, triethylamine, ethanolamine, tris (hydroxymethyl) aminomethane, etc. The sodium salts can also be conveniently prepared by treating a solution of the acid in ethyl acetate with an excess of sodium-2-ethyl hexanoate.

The compounds of III and IV, and salts thereof, have a broad spectrum of antibacterial activity against both gram positive and gram negative organisms such as Staphylococcus aureus, Proteus vulgaris, Escherichia coli, Streptococcus pyogenes, Klebsiella pneumoniae, and Shigella sonnei. The compounds can be used to combat or prophylactically to prevent infections of this nature in mammals and can be administered in the same manner as cephalothin or cephalosporin derivative drugs are generally administered (typically parenterally or orally). The compounds can be administered in a wide variety of dosage forms, either alone or in combination with other pharmaceutically compatible medicaments, in the form of pharmaceutical compositions suited for oral or parenteral administration. The dosage forms typically comprise the compounds (typically as pharmaceutically acceptable salts) and a pharmaceutically carrier and are preferably formulated in unit dosage form to facilitate the simple administration of precise dosages. The pharmaceutical carrier can be either a solid material or liquid, in which the compound is dissolved, dispersed or suspended. The dosage form can optionally contain other compatible medicaments, preservatives, emulsifying agents, wetting agents and/or pH-buffering agents. Suitable preservatives which can be used include, for example, benzyl alcohol and the like. Suitable buffering agents include, for example, sodium acetate and pharmaceutical phosphate salts and the like. Liquid dosage forms include, for example, solutions, suspensions, emulsions, syrups, elixirs, etc. Liquid carriers include, for example, water, saline solution, etc. Solid dosage forms include, for example, tablets, powders, capsules, pills, etc. Suitable solid carriers include, for example, pharmaceutical grades of starch, lactose, sodium saccharin, sodium bisulfite and the like.

The compounds of this invention are typically administered in dosages of about from 10 to 100 mg. per kg. per day of body weight. The precise effective dosage will, of course, vary depending upon the mode of administration, the condition being treated and the host.

The compounds can also be used as antiseptic agents in cleaning or disinfecting compositions, typically in solution form or suspended in a liquid carrier or in an aerosol spray.

Definitions

The following terms, as used hereinabove and below, have the following meaning unless expressly stated to the contrary. The term lower alkyl refers to alkyls having from one through six carbon atoms and includes both straight chain and branched chain alkyls such as, for example, methyl, ethyl, isopropyl, t-butyl, pentyl, n-hexyl, isohexyl, and the like. The term lower alkoxy refers to alkoxy groups having from one through six carbon atoms and can be defined as the group -OR' wherein R' is lower alkyl as defined hereinabove. The term halo or halide refers to the group of fluoro, chloro, bromo, and iodo or the corresponding halides. The term pharmaceutically acceptable salts refers to those salts of the parent compound which do not significantly adversely affect the pharmaceutical properties (e.g. toxicity, effectiveness, etc.) of the parent compound such as, for example, are conventionally used in the pharmaceutical art. The salts of the present invention are pharmaceutically acceptable cation salts, with respect to the acid and sulfo moieties of the compounds of formulas III and IV, and in case of formula III wherein $R^4$ is carboxy or sulfo can be prepared as both mono and bis salts. Suitable pharmaceutically acceptable cations include, for example, the alkali metals, e.g. sodium, potassium, etc.; alkali earth metals, e.g. calcium, etc.; ammonia; organic salts of triethylamine, diethylamine, tris(hydroxymethyl)aminomethane, ethanolamine, choline, caffeine and the like. The term 1-methyltetrazol-5-yl refers to the radical having the formula

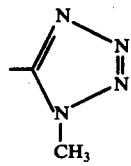

and the term 1,2,4-triazol-5-yl refers to the radical having the formula

The term room temperature refers to about 20° Centigrade and all temperatures and temperature ranges refer to degrees centigrade. All percents refer to weight percents and the term equivalent mole amount refers to an amount stoichiometrically equivalent to the other reactant in the reaction referred to.

The term benzhydryl refers to the radical diphenylmethyl, i.e.

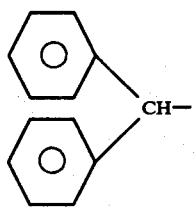

A further understanding of the invention can be had from the following non-limiting preparations and examples. Wherein proton magnetic resonance spectrum (n.m.r.) are determined at 100 mHz (the signs of the coupling constants are not assigned) and signals are assigned as singlets (s), broad singlet (bs), doublets (d), double doublets (dd), triplets (t), double triplets (dt), quartets (q) and multiplets (m).

PREPARATION 1

3-Acetoxymethyl-7β-(thiophen-2-yl-acetamido)-ceph-2-em-4-carboxylic acid.

In this preparation 42 g. of cephalothin (i.e. 3-acetoxymethyl-7β-(thiophen-2-yl-acetamido)-ceph-3-em-4-carboxylic acid) is dissolved with warming in 130 ml. pyridine, and then cooled to about 18° C. 13 Ml. of acetic anhydride is added and the resulting mixture allowed to stand for two hours at room temperature affording a crystalline precipitate. Then 250 ml. of a 65:35, by vol., ethyl ether/ethyl acetate mixture is added and the resulting mixture stirred for one hour and then filtered. The recovered crystals are washed with 65 ml. of 65:35, by vol., ethyl acetate/ethyl ether solution and dried under vacuum to give 41 g. of the pyridinium salt of 3-acetoxymethyl-7β-(thiophen-2-yl-acetamido)-ceph-2-em-4-carboxylic acid. This salt is added to a mixture of 650 ml. water and 650 ml. ethyl acetate and the mixture then acidified to pH 2 using 20% aqueous hydrochloric acid. The ethyl acetate layer is separated and the aqueous layer further extracted with 400 ml. ethyl acetate. The combined ethyl acetate extracts are washed twice with brine, dried over anhydrous sodium sulfate and the solvent then removed under reduced pressure to afford 34 g. of 3-acetoxymethyl-7β-(thiophen-2-yl-acetamido)-ceph-3-em-4-carboxylic acid.

PREPARATION 2

3-Hydroxymethyl-7β-(thiophen-2-yl-acetamido)-ceph-2-em-4-carboxylic acid.

In this preparation 34 g. of 3-acetoxymethyl-7β-(thiophen-2-yl-acetamido)-ceph-2-em-4-carboxylic acid is added to a solution of 8.4 g. of lithium hydroxide monohydrate in 1000 ml. of water. The mixture is stirred at room temperature under nitrogen for two hours and then layered with 600 ml. of ethyl acetate. The pH of the mixture is then readjusted to pH 2 by the addition of 20% aqueous hydrochloric acid (~50 ml.). The ethyl acetate layer is separated and the aqueous layer is extracted twice with 500 ml. portions of ethyl acetate. The combined ethyl acetate extracts are washed twice with brine, dried over anhydrous sodium sulfate and evaporated to dryness under reduced pressure affording 24.2 g. of 3-hydroxymethyl-7β-(thiophen-2-yl-acetamido)-ceph-2-em-4-carboxylic acid.

PREPARATION 3

Benzhydryl 3-hydroxymethyl-7β-(thiophen-2-yl-acetamido)-ceph-2-em-4-carboxylate.

In this preparation 24.2 g. of 3-hydroxymethyl-7β-(thiophen-2-yl-acetamido)-ceph-2-em-4-carboxylic acid is dissolved in 800 ml. of tetrahydrofuran, and then with 15 g. of diphenyldiazomethane is added and the resulting mixture stirred at room temperature for three hours. The mixture is evaporated to dryness under reduced pressure and 250 ml. of 90:10, vol., ethyl ether/methylene chloride solution is added to the residue. After the mixture is stirred for four hours, the solid is recovered by filtration, and washed with 100 ml. of 90:10 ethyl ether/methylene chloride and then dried affording 28.5 g. of benzhydryl 3-hydroxymethyl-7β-(thiophen-2-yl-acetamido)-ceph-2-em-4-carboxylate.

PREPARATION 4

Benzhydryl 3-formyl-7β-(thiophen-2-yl-acetamido-ceph-2-em-4-carboxylate.

In this preparation 31 g. of dried chromium trioxide is added to a mixture of 51 g. of dry pyridine and 800 ml. of dry methylene chloride and stirred at 15° C under nitrogen for 20 minutes. 26 Grams of benzhydryl 3-hydroxymethyl-7β-(thiophen-2-yl-acetamido)-ceph-2-em-4-carboxylate in 250 ml. of dry methylene chloride is added in one portion. The resulting mixture is stirred for 30 minutes and then filtered through diatomaceous earth. The contents of the reaction flask and the diatomaceous earth are washed with 500 ml. of methylene chloride and combined with the preceding filtrate and then washed with 400 ml. of 5% aqueous potassium hydroxide solution, 500 ml. of 20% aqueous hydrochloric acid and twice with 400 ml. brine. The aqueous washings are back extracted with 500 ml. of methylene chloride and the extracts added to the previously washed methylene chloride filtrate, then dried over sodium sulfate and then stirred for one hour with 30 g. of silica gel. The mixture is filtered and the silica gel washed with 400 ml. 1:1 vol. ethyl acetate/methylene chloride. The combined filtrates are evaporated to dryness under reduced pressure and the resulting residue (26 g.) is recrystallized from ethyl ether/methylene chloride affording 21.4 g. of benzhydryl 3-formyl-7β-(thiophen-2-yl-acetamido)-ceph-2-em-4-carboxylate.

EXAMPLE 1

This example illustrates step 1 of the process of the invention for preparing the compounds of the invention. In this example 2.5 g. of benzhydryl 3-formyl-7β-(thiophen-2-yl-acetamido)-ceph-2-em-4-carboxylate in 50 ml. of anhydrous tetrahydrofuran is stirred under nitrogen at −70° C and 10 ml. of 2.5 molar solution of vinyl magnesium chloride is added dropwise over five minutes. After 15 minutes, 50 ml. of pH 7 buffer solution of dibasic sodium phosphate and monobasic potassium phosphate is added to the well stirred mixture, and then warmed to room temperature. The mixture is diluted with 200 ml. of water and layered with 200 ml. of ethyl acetate. The pH of the aqueous layer is adjusted to pH 4 by the addition of 20% aqueous hydrochloric acid. The ethyl acetate layer is separated and the aqueous layer extracted with 100 ml. ethyl acetate. The ethyl acetate extracts are combined and then washed twice with 50 ml. portions of brine, dried over sodium sulfate and evaporated under reduced pressure affording benzhydryl 3-(1-hydroxyprop-2-enyl)-7β-(thiophen-2-yl-acetamido)-ceph-2-em-4-carboxylate as a pale yellow oil (2.7 g.).

The two isomers (α-hydroxy and β-hydroxy) are separated using thick-layer or column chromatography on silica gel using 45:5 vol./vol. of methylene chloride/acetone. They are then characterized by their nmr spectra (both oils).

Isomer 1 (higher Rf), nmr (CDCl$_3$) δ:3.78s, 2H

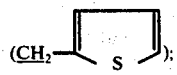

4.596bd, J 14Hz, 1H (HC-OH); 4.9–5.7m, 6H (H-6, H-7, H-4 + CH=CH$_2$); 6.366s, 1H (H-2); 6.7–7.5m, 14H (CHφ$_2$ +

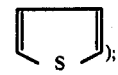

Isomer 2 (lower Rf), nmr (CDCl$_3$) δ:3.79s, 2H

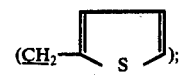

4.63m, 1H (HC-OH); 5.0–5.8m, 6H (H-6, H-7, H-4 + CH=CH$_2$); 6.25s, 1H (H-2); 6.8–7.5m, 14H (CHφ$_2$ +

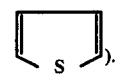

EXAMPLE 2

This example illustrates step 2 of the process of the invention for preparing the compounds of the invention. In this example, a 2.7 g. of the benzhydryl 3-(1-hydroxyprop-2-enyl)-7β-(thiophen-2-yl-acetamido)-ceph-2-em-4-carboxylate is dissolved in 30 ml. tetrahydrofuran and stirred at 40° C, and 5-mercapto-1-methyl-tetrazole (0.6 g.) and about 50 mg. of p-toluenesulfonic acid are added. The mixture is stirred for 5 hours at 40° C, then poured into 200 ml. of saturated aqueous sodium bicarbonate solution and extracted twice with 200 ml. portions of ethyl acetate. The ethyl acetate extracts are combined and washed with brine, dried over sodium sulfate and evaporated to dryness under reduced pressure affording 2.8 g. of an orange oil. This was chromatographed on 200 g. of silica gel eluting with 6:4 vol. ratio of ethyl acetate/hexane. The fractions which are homogeneous by thin-layer chromatography are combined affording 2.1 g. of the benzhydryl 3-[3-(1-methyl-tetrazol-5-ylthio)-prop-1-(t)-enyl]-7β-(thiophen-2-yl-acetamido)-ceph-2-em-4-carboxyl-ate as a pale yellow glass, [α]$_D$ (CHCl$_3$) + 321°; uv (EtOH) 284 nm (ε21,600); ir (KBr) 1780, 1740, 1675 cm$^{-1}$; nmr (CDCl$_3$); 3.80s, 3H (N-Me); 3.82s 2H

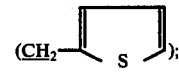

∼3.8, 2H (CH$_2$-S, hidden by preceding signals); 5.2, 2H (H-6 + H-45.56dd, J 4,8Hz, 1H (H-7); 5.7dt, J 7,16Hz, 1H (H-2'); 6.2d, J 16Hz, 1H (H-1'); 6.27s, 1H (H-2); 6.51d, J 8Hz, 1H (N-H); 6.8–7.4m, 14H (CHφ$_2$ +

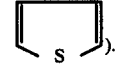

Similarly, benzhydryl 3-[3-(1,2,4-triazol-5-ylthio)-prop-1-(t)-enyl]-7β-(thiophen-1-yl-acetamido)-ceph-2-em-4-carboxylate (oil, nmr (CDCl$_3$):360d, J 7Hz, 2H (3'-CH$_2$), 3,82s, 2H

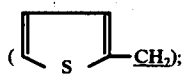

5.16d, J 4.5Hz, 1H (H-6); 5.20s, 1H (H-4); 5.49dd, J 4.5, 8Hz, 1H (H-7); 5.69dt, J 16, 7 Hz, 1H (H-2'); 5.98d, J 16Hz, 1H (H-1')6.14s, 1H (H-2); 6.83s, 1H (C$H\phi_2$); 6.9-7.4m, 13H ($\phi_2$ +

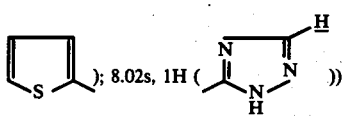); 8.02s, 1H ( ))

is prepared by following the same procedure but using 5-mercapto-1,2,4-triazole in place of 5-mercapto-1-methyltetrazole.

EXAMPLE 3

This example illustrates step 3 of the process of the invention for preparing the compounds of the invention. In this example, a solution of 0.9 g. of the benzhydryl 3-[3-(1-methyltetrazol-5-ylthio)-prop-1-(t)-enyl]-7β-(thiophen-2-yl-acetamido)-ceph-2-em-4-carboxylate in 5 ml. of dry pyridine is treated with 0.1 ml. of triethylamine. The mixture is allowed to stand at room temperature for 20 hours and then evaporated to dryness under reduced pressure. The resulting residue is chromatographed on 100 g. of silica gel eluting with 15% vol. ethyl acetate/benzene affording 300 mg. of benzhydryl 3-[3-(1-methyltetrazol-5-ylthio)-prop-1-(t)-enyl]-7β-(thiophen-2-yl-acetamido)-ceph-3-em-4-carboxylate and 500 mg. of the starting material of benzhydryl 3-[3-(1-methyltetrazol-5-ylthio)-prop-1-(t)-enyl]-7β-(thiophen-2-yl-acetamido)-ceph-2-em-4-carboxylate. The recovered starting material is treated in the same manner as above, affording another 150 mg. of benzhydryl 3-[3-(1-methyltetrazol-5-ylthio)-prop-1-(t)-enyl]-7β-(thiophen-2-yl-acetamido)-ceph-3-em-4-carboxylate and 250 mg. of recovered benzhydryl 3-[3-(1-methyltetrazol-5-ylthio)-prop-1-(t)-enyl]-7β-(thiophen-2-yl-acetamido)-ceph-2-em-4-carboxylate; white solid, m.p. 90-95° (dec.); $[\alpha]_D$ −158° (CHCl$_3$); uv (EtOH):301 nm (ε19,400); ir (KBr): 1785, 1720, 1680cm$^{-1}$;nmr (CDCl$_3$):3.4m, 2H (2-CH$_2$); 3.80s, 2H 3.83s, 3H (N-Me); 3.91d, J 7.5Hz, 2H (3'-CH$_2$); 4.95d, J 4.5Hz, 1H (H-6); 5.79dd, J 4.5, 9 Hz, 1H (H-7); 6.08dt, J 16, 7.5Hz, 1H (H-2'); 6.63d, J 9Hz, 1H); 6.8-7.5m, 15H (CH$\phi_2$ +

+ H-1'). Anal. Found: C, 58.06; H, 4.65; N, 12.58. C$_{31}$H$_{28}$N$_6$O$_4$S$_3$ requires C, 57.75; H, 4.38; N, 13.03.

Similarly, benzhydryl 3-[3-(1,2,4-triazol-5-ylthio)-prop-1(t)-enyl]-7β-(thiophen-2-yl-acetamido)-ceph-3-em-4-carboxylate (m.p. 183-185°; $[\alpha]_D$-87° (dioxane); uv (EtOH) 306 nm (ε19,100); ir (KBr) 1790, 1705, 1665cm$^{-1}$; nmr (DMSO−d$_6$); 3.33bs, 2H (2-CH$_2$); 3.69d, J 7Hz, 2H (3'-CH$_2$); 3.79s, 2H 5.20d, J 4.5Hz, 1H (H-6); 5.75dd, J 4.5, 8 Hz, 1H (H-7); 6.22dt, J 16, 7 Hz, 1H (H-2'); 6.69d, J 16Hz, 1H (H-1'); 6.9-7.6m, 13H ($\phi_2$ +

); 8.39s, 1H ( ).

Analysis Found: C, 58.93; H, 4.55; N, 10.96. C$_{31}$H$_{27}$N$_5$O$_4$S$_3$ requires C, 59.13; H, 4.32; N, 11.12%) is prepared by following the same procedure but using benzhydryl 3-[3-(1,2,4-triazol-5-ylthio)-prop-1-(t)-enyl]-7β-(thiophen-2-yl-acetamido)-ceph-2-em-4-carboxylate in place of benzhydryl 3-[3-(1-methyltetrazol-5-ylthio)-prop-1-(t)-enyl]-7β-(thiophen-2-yl-acetamido)-ceph-2-em-4-carboxylate.

EXAMPLE 3A

This example illustrates step 3a of the process of the invention for preparing the compounds of the invention. In this example, 1.0 g. of benzhydryl 3-[3-(1-methyltetrazol-5-ylthio)-prop-1-(t)-enyl]:7β-(thiophen-2-yl-acetamido)-ceph-2-em-4-carboxylate in 25 m. of methylene chloride was stirred at 0° C and m-chloroperbenzoic acid (0.3 g.) is added in portions over two hours. The mixture is further diluted with methylene chloride and washed with excess dilute aqueous sodium bicarbonate solution, dried over anhydrous sodium sulfate and evaporated under reduced pressure to give a yellow foam. This is chromatographed on silica gel, eluting with acetone/methylene chloride 15:85 vol. The pure fractions are combined affording 0.6 g. of the benzhydryl 3-[3-(1-methyltetrazol-5-ylthio)-prop-1-(t)-enyl]-7β-(thiophen-2-yl-acetamido)-ceph-3-em-4-carboxylate-1-oxide as a white crystalline solid, m.p. 125°-127° C; $[\alpha]_D$−204° (CHCl$_3$); uv (EtOH) 307 nm (ε20,200); ir (KBr) 1790, 1720, 1680 cm$^{-1}$; nmr (CDCl$_3$) 3.06d, 3.95d, J 19Hz, 2H (H-2α and H-2β); 3,82s, 2H 3.85s, 3H (N-Me); 3.92d, J 7 Hz (3'-CH$_2$); 4.47d, J 4.5 H$_z$ (H-6); 5.9-6.3m, 2H (H-7 and H-2'); 6.8-7.6m, 16H (CH$\phi_2$ +

+ H-1' + NH). Anal. Found: C, 56.16; H, 4.18; N, 12.49. C$_{31}$H$_{28}$H$_6$O$_5$S$_3$ requires C, 56.35; H, 4.27; N, 12.72.

Similarly, benzhydryl 3-[3-(1,2,4-triazol-5-ylthio)-prop-1-(t)-enyl]-7β-(thiophen-2-yl-acetamido)-ceph-3-em-4-carboxylate-1-oxide is prepared by following the same procedure but using benzhydryl 3-[3-(1,2,4-triazol-5-ylthio)-prop-1-(t)-enyl]-7β-(thiophen-2-ylacetamido)-ceph-2-em-4-carboxylate as the starting material.

EXAMPLE 3B

This example illustrates step 3b of the process of the invention for preparing the compounds of the invention. In this example, 0.5 g. of the benzhydryl 3-[3-(1-methyltetrazol-5-ylthio)-prop-1-(t)-enyl]-7β-(thiophen-2-yl-acetamido)-ceph-3-em-4-carboxylate-1-oxide is dissolved in 10 ml. of dry dimethylformamide and the solution stirred at 0° C under nitrogen while stannous chloride (0.5 g.) and acetyl chloride (1 ml.) are added and is stirred at 0° C for 15 minutes. Stirring is continued while the solution is warmed to room temperature and continued for another 20 minutes. The mixture is then diluted with water and extracted twice with ethyl acetate. The combined extracts are washed twice with water and brine, dried over sodium sulfate and evaporated under reduced pressure affording a 0.6 g. of a yellow oil. This is chromatographed on silica gel eluting with acetone/methylene chloride (5:95 vol.) yielding 0.40 g. of the benzhydryl 3-[3-(1-methyltetrazol-5-ylthio)-prop-1-(t)-enyl]-7β-(thiophen-2-yl -acetamido)-ceph-3-em-4-carboxylate as a white crystalline solid.

Similarly, benzhydryl 3-[3-(1,2,4-triazol-5-ylthio)-prop-1-(t)-enyl]-7β-(thiophen-2-yl-acetamido)-ceph-3-em-4-carboxylate is prepared by following the same procedure but using benzhydryl 3-[3-(1,2,4-triazol-5-ylthio)-prop-1-(t)-enyl]-7β-(thiophen-2-yl-acetamido)-ceph-3-em-4-carboxylate-1-oxide as the starting material.

EXAMPLE 4

This example illustrates step 4 of the process of the invention for preparing the compounds of the invention. In this example, 0.25 g. of the benzyhydryl 3-[3-(1-methyltetrazol-5-ylthio)-prop-1-(t)-enyl]-7β-(thiophen-2-yl-acetamido)-ceph-3-em-4-carboxylate is stirred at room temperature under nitrogen in 6 ml. of dry methylene chloride and 60 μl. of pyridine and 100 mg. of phosphorous pentachloride are added. The mixture is stirred for two hours at room temperature, then cooled to 0° C and 0.1 ml. of isobutyl alcohol is added and stirring continued for 40 minutes. Then 0.5 ml. of water is added and the mixture was stirred vigorously for 15 minutes. The mixture is then diluted with excess dilute aqueous sodium bicarbonate solution and extracted twice with ethyl acetate. The combined extracts are washed with water and brine, dried over sodium sulfate, and evaporated under reduced pressure affording the crude benzhydryl 3-[3-(1-methyltetrazol-5-ylthio)-prop-1-(t)-enyl]-7β-amino-ceph-3-em-4-carboxylate as a brown oil; nmr (CDCl$_3$) 3.51m, 2H (2-CH$_2$); 3.85s, 3H (N-Me); ~3.9, 2H (3'-CH$_2$, overlapped by N-Me; 3.75d, 3.95d, J 51, 2H (H-6 + H-7); 6.1dt, J 16, 7.5 Hz, 1H (H-2'); 6.88d, J 16 Hz, 1H (H-1'); 7.04s, 1H (CHφ$_2$); 7.1–7.6m, 10H (φ$_2$).

Similarly, benzhydryl 3-[3-(1,2,4-triazol-5-ylthio)-prop-1-(t)-enyl]-7β-aminoceph-3-em-4-carboxylate is prepared by following the same procedure using benzhydryl 3-[3-(1,2,4-triazol-5-ylthio)-prop-1-(t)-enyl]-7β-(thiophen-2-yl-acetamido)-ceph-3-em-4-carboxylate as the starting material.

EXAMPLE 5

This example illustrates step 5 of the process of the invention. In this example, 0.5 ml. of pyridine and 0.1 ml. of α-dichloroacetoxyphenacetyl chloride are added to a stirring mixture containing 0.1 g. of diphenylmethyl 7β-amino-3-[3-(1-methyltetrazol-5-ylthio)-prop-1-(t)-enyl]-ceph-3-em-4-carboxylate in 5 ml. of chloroform at 0° C. The mixture is stirred for 15 minutes, then diluted with excess dilute aqueous hydrochloric acid and extracted twice with ethyl acetate. The combined ethyl acetate extracts are washed with dilute aqueous sodium bicarbonate solution and brine, dried over sodium sulfate and evaporated under reduced pressure to give a brown oil (0.25 g.). Thick-layer chromatography of this oil on silica gel eluting with ethyl acetate/hexane 6:4 vol. yields 0.15 g. of diphenylmethyl 3-[3-(1-methyltetrazol-5-ylthio)-prop-1-(t)-enyl]-7β-D-(α-dichloroacetoxy-α-phenylacetamido)-ceph-3-em-4-carboxylate. This is dissolved in 0.5 ml. anisole (0.5 ml.) and stirred at 0° C while 3 ml. of trifluoroacetic acid is added. After five minutes, the mixture is evaporated to dryness and the resulting residue taken up in ethyl acetate. The ethyl acetate solution is extracted with two 10 ml. portions of saturated aqueous sodium bicarbonate solution. The combined extracts are stirred at room temperature for two hours, then acidified using dilute aqueous hydrochloric acid and then extracted twice with ethyl acetate. The combined ethyl acetate extracts are washed with brine and dried over sodium sulfate. The solution is then treated with 0.1 g. of diphenyldiazomethane and stirred at room temperature for 2 hours. The solvent is removed by evaporation under reduced pressure and the residue purified using thick-layer chromatography on silica gel eluting with ethyl acetate/benzene 6:4, affording 105 mg. of diphenylmethyl 3-[3-(1-methyltetrazol-5-ylthio)-prop-1-(t)-enyl]-7β-D-(α-hydroxy-α-phenylacetamido)-ceph-3-em-4-carboxylate as a white solid, m.p. 95°–100° C (dec.); [α]$_D$-161° (CHCl$_3$); uv (EtOH) 305 nm (ε 18,700); ir (KBr):1785, 1725, 1685 cm$^{-1}$; nmr (CDCl$_3$):3.43m, 2H (2-CH$_2$); 3.82s, 3H (N-Me); 3.83d, J 7.5 Hz, 2H (3'-CH$_2$); 4.94d, J 5 Hz, 1H (H-6), 5.11s, 1H (CH-OH); 5.73dd, J 5, 9 Hz, 1H (H-7); 6.07dt, J 16, 7.5 Hz, 1H (H-2'); 6.92d, J 16 Hz, 1H (H-1'); 6.97s, 1H (CHφ$_2$); 7.1-7.5m, 15H (CHφ$_2$ + HO-CHφ). Anal. Found: C, 60.35, H, 4.79; N, 12.31. C$_{33}$H$_{30}$N$_6$O$_5$S$_2$ requires C, 60.54; H, 4.62; N, 12.84.

Similarly, diphenylmethyl 7β-D-(α-hydroxy-α-phenylacetamido)-3-[3-(1,2,4-triazol-5-ylthio)-prop-1-(t)-enyl]-ceph-3-em-4-carboxylate is prepared by following the same procedure but using diphenylmethyl 7β-amino-3-[3-(1,2,4-triazol-5-ylthio)-prop-1-(t)-enyl]-ceph-3-em-4-carboxylate as the starting material.

EXAMPLE 5A

This example illustrates step 5 of the process of the invention. In this example, 0.1 g. of α-(t-butoxycarbonyl)-α-phenylacetic acid and 0.15 g. of dicyclohexylcarbodiimide are added to a mixture of 0.1 g. of diphenylmethyl 7β-amino-3-[3-(1-methyltetrazol-5-ylthio)-prop-1-(t)-enyl]-ceph-3-em-4-carboxylate in 10 ml. of dichloromethane, then stirred at room temperature for 4 hours and then 2 ml. of a saturated solution of oxalic acid in methanol is added. After 10 minutes, the mixture is filtered and the filtrate recovered and diluted with ethyl acetate, then washed with aqueous sodium bicarbonate solution, then brine, and then dried over sodium sulfate and evaporated to dryness under reduced pressure. The residue is purified using thick-layer chromatography on silica gel developing with 5% vol. acetone:dichloromethane affording diphenylmethyl 7β-(α-t-butoxycarbonyl-α-phenylacetamido)-3-[3-(1-methyltetrazol-5-ylthio)-prop-1-(t)-enyl]-ceph-3-em-4-carboxylate, as a pale yellow oil, uv (EtOH); 305 nm (ε 14,250); ir (CHCl$_3$) 1790, 1720, 1680cm$^{-1}$; nmr (CDCl$_3$) 1.41s, 143s (9H total, t-Bu for each diastereoisomer); 3.46bs, 2H (2-CH$_2$); 3.85s, 3H (N-Me); ca 3.9d, J8, 2H (3'-CH$_2$); 4.41s, 4.46s (1H total, C$\underline{H}$-CO$_2$ t-Bu for each isomer); 4.95d, 4.99d, J 4.5 Hz (H-6 in each isomer); ca 5.8m, 1H (H-7); 6.1dt, J 8, 17 Hz, 1H (H-2'); 6.98s, 1H (C$\underline{H}$φ$_2$); 6.98d, J 17 Hz, 1H (H-1'), 7.1-7.6m, 15H (aromatic H).

Similarly, diphenylmethyl 7β-(α-t-butoxycarbonyl-α-phenylacetamido)-3-[3-(1,2,4-triazol-5-ylthio)-prop-1-(t)-enyl]-ceph-3-em-4-carboxylate is prepared by following the same procedure but using diphenylmethyl 7β-amino-3-[3-(1,2,4-triazol-5-ylthio)-prop-1-(t)-enyl]-ceph-3-em-4-carboxylate.

EXAMPLE 5B

This example illustrates step 5 of the process of the invention. In this example, a mixture containing 0.1 g. of diphenylmethyl 7β-amino-3-[3-(1-methyltetrazol-5-ylthio)-prop-1-(t)-enyl]-ceph-3-em-4-carboxylate; 0.1 g. of D-(−)-α-(t-butoxycarbonylamino)-α-phenylacetic acid and 0.15 g. of dicyclohexylcarbodiimide in 5 ml. of dichloromethane is stirred at room temperature for two hours and then 2 ml. of a saturated solution of oxalic acid in methanol is added. After ten minutes, the mixture is filtered. The filtrate is diluted with ethyl acetate, washed successively with sodium bicarbonate solution and brine, dried over sodium sulfate and then evaporated to dryness. The resulting oil is subjected to thick-layer chromatography on silica gel developing with 5% acetone/dichloromethane, affording diphenylmethyl 7β-D-[α-(t-butoxycarbonylamino)-phenylacetamido]-3-[3-(1-methyltetrazol-5-ylthio)-prop-1-(t)-enyl]-ceph-3-em-4-carboxylate as a white crystalline solid; m.p. 115°-117° C, [α]$^D$ -151° (CHCl$_3$); uv (EtOH) 305 nm (ε 18,800); ir (KBr) 1788, 1720, 1690, 1665 cm$^{-1}$; nmr (CDCl$_3$):1.41s, 9H (tBu); 3.39bs, 2H (2-CH$_2$); 3.85s, 3H (N-Me); 3.89d, J 7.5 Hz, 2H (3'-CH$_2$); 4.93d, J 5 Hz, 1H (H-6); 5.21d, J 6 Hz, 1H (CHNHCO$_2$ t-Bu); 5.79dd, J 4.5, 9 Hz, 1H (H-7); 6.07dt, J 16, 7.5 Hz, 1H (H-2'; 6.92d, J 16 Hz, 1H (H-1'); 6.98s, 1H (C$\underline{H}$φ$_2$); 7.1-7.6m, 15H (aromatic H). Analysis Found: C, 60.61; H, 5.14; N, 12.97. C$_{38}$H$_{39}$N$_7$O$_6$S$_2$ requires C, 60.54; H, 5.22; N, 13.01%.

Similarly, by following the same procedure but respectively replacing D-(−)-α-(t-butylcarbonylamino)-α-phenyl-acetic acid with D-(−)-α-(t-butylcarbonylamino)-α-(p-hydroxyphenyl)-acetic acid, the following compounds are respectively prepared:

diphenylmethyl 7β-D-[α-(t-butoxycarbonylamino)-α-(p-hydroxyphenyl)-acetamido]-3-[3-(1-methyltetrazol-5-ylthio)-prop-1-(t)-enyl]-ceph-3-em-4-carboxylate; m.p. 130°-135° (decomp.); [α]$_D$ -125° (CHCl$_3$); uv (EtOH) 303nm (ε 15100); ir (KBr) 1790, 1720, 1685 cm$^{-1}$; nmr (CDCl$_3$):1.38s, 9H (tBu); 3.28s, 2H (2-CH$_2$); 2.78s, 3H (N-Me); ~3.8, 2H (3'-CH$_2$, overlapping N-Me); 4.8d, J 4.5Hz, 1H (H-6); 5.13d, J 6Hz, 1H (C$\underline{H}$NHCO$_2$tBu); 5.72dd, J 4.5, 9 Hz, 1H (H-7); 6.02dt, J 7, 16 Hz, 1H (H-2'); 6.5-7.5m, ~16H (φ$_2$CH,

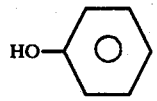

+ H-1'); and diphenylmethyl 7β-D-[α-(t-butoxycarbonylamino)-α-(p-hydroxyphenyl)-acetamido]-3-[3-(1,2,4-triazol-5-ylthio)-prop-1-(t)-enyl]-ceph-3-em-4-carboxylate.

EXAMPLE 6

This example illustrates step 6 of the process of the invention, and the in situ preparation of the salts of the invention. In this example, 2.5 ml. of trifluoroacetic acid is added to a stirring mixture containing 0.1 g. of diphenylmethyl 3-[3-(1-methyltetrazol-5-ylthio)-prop-1-(t)-enyl]-7β-D-(α-hydroxy-α-phenylacetamido)-ceph-3-em-4-carboxylate and 0.5 ml. of anisole at 0° C. The resulting mixture is stirred vigorously, at 0° C, for 5 minutes and then evaporated to dryness under reduced pressure. The residue is dissolved in tetrahydrofuran, filtered, and the filtrate (containing 7β-D-(α-hydroxy-α-phenylacetamido)-3-[3-(1-methyltetrazol-5-ylthio)-prop-1-(t)-enyl]-ceph-3-em-4-carboxylic acid is added to an excess of a solution sodium 2-ethylhexanoate in tetrahydrofuran. The resulting mixture is evaporated to dryness under reduced pressure and the residue mixed with to 5 ml. of isopropanol affording a white precipitate. The precipitate is collected by filtration, washed with two portions of isopropanol, and then dried under reduced pressure affording 30 mg. of the sodium salt of 7β-D-(α-hydroxy-α-phenylacetamido)-3-[3-(1-methyltetrazol-5-ylthio)-prop-1-(t)-enyl]-ceph-3-em-4-carboxylate; white powder, m.p. 180°-190° C (decomposition) uv (H$_2$O) 295 nm (ε 17,700); ir (KBr) 1760, 1725, 1600 cm$^{-1}$; nmr (DMSO-d$_6$):3.39bs, 2H (2-CH$_2$); 3.93s, 3H (N-Me); 3.99d, J 7.5 Hz, 2H (3'-CH$_2$); 4.98d, J 4.5 Hz, 1H (H-6); 5.11s, 1H (C$\underline{H}$-OH); 5.52dd, J 9, 4.5 Hz, 1H (H-7), 5.72dt, J 16, 7.5 Hz, 1H (H-2'); 7.09d, J 16 Hz, 1H (H-1'); 7.1-7.6m, 5H (φ−); 8.58d, J 9, 1H (NH).

Similarly, the sodium salt of 7β-D-(α-hydroxy-phenylacetamido)-3-[3-(1,2,4-triazol-5-ylthio)-prop-1-(t)-enyl]-ceph-3-em-4-carboxylate is prepared by following the same procedure but using diphenylmethyl 3-[3-(1,2,4-triazol-5-ylthio)-prop-1-(t)-enyl]-7β-D-(α-hydroxy-α-phenylacetamido)-ceph-3-em-4-carboxylate as the starting material.

For purposes of purifying and isolating the free acids, a small portion (10 mg.) of each sodium salt is converted back to the 4-carboxylic acid by dissolving in water, adjusting the pH to 1.5 using dilute hydrochloric acid and extracting twice with ethyl acetate. The combined extracts are washed with brine, dried and evaporated to dryness. The residue is mixed with ethyl ether and the 4-carboxylic acid collected by filtration.

EXAMPLE 6A

This example illustrates step 6 of the process of the invention and the in situ preparation of the salts of the invention. In this example, 2.5 ml. of trifluoroacetic acid is added to a mixture containing 0.1 g. of diphenylmethyl 7β-(α-t-butoxycarbonyl-α-phenylacetamido)-3-[3-(1-methyltetrazol-5-ylthio)-prop-1-(t)-enyl]-ceph-3-em-4-carboxylate and 0.5 ml. of anisole at 0° C and vigorously stirred at this temperature for 30 minutes. The mixture is evaporated to dryness, under reduced pressure, and the residue then washed twice with ethyl ether and then dissolved in ethyl acetate, and then filtered affording a filtrate containing 7β-(α-carboxy-α-phenylacetamido)-3-[3-(1-methyltetrazol-5-ylthio)-prop-1-(t)-enyl]-ceph-3-em-4-carboxylic acid. The filtrate is then treated with an excess of sodium 2-ethylhexanoate in ethyl acetate and then evaporated to dryness under reduced pressure. The residue is stirred with 5 ml. of isopropanol for one hour, then filtered, the residue recovered, washed twice with isopropanol, once with ethyl acetate, then dried under vacuum, affording 55 mg. of 7β-(α-carboxy-α-phenylacetamido)-3-[3-(1-methyltetrazol-5-ylthio)-prop-1-(t)-enyl]-ceph-3-em-4-carboxylic acid disodium salt as an off-white powder; m.p. 160° C (decomposition, darkened above ca. 140° C); uv (H₂O) 297 nm (ε 17,590); ir KBr 1765, 1670, 1600 cm⁻¹.

Similarly, the sodium salt of 7β-(α-carboxy-α-phenylacetamido)-3-[3-(1,2,4-triazol-5-ylthio)-prop-1-(t)-enyl]-ceph-3-em-4-carboxylic acid is prepared by following the same procedure but using diphenylmethyl 7β-(α-t-butoxycarbonyl-α-phenylacetamido)-3-[3-(1,2,4-triazol-5-ylthio)-prop-1-(t)-enyl]-ceph-3-em-4-carboxylate as the starting material.

For purposes of purifying and isolating the free acids, a small portion (10 mg.) of each sodium salt is converted back to the 4-carboxylic acid by dissolving in water, adjusting the pH to 1.5 using dilute hydrochloric acid and extracting twice with ethyl acetate. The combined extracts are washed with brine, dried and evaporated to dryness. The residue is mixed with ethyl ether and the 4-carboxylic acid collected by filtration.

EXAMPLE 6B

This example illustrates methods according to step 6 of the process of the invention. In this example, 3 ml. of trifluoroacetic acid is added to a stirring mixture of 0.15 g. of diphenylmethyl 7β-D-[α-(t-butoxycarbonylamino)-α-phenylacetamido]-3-[3-(1-methyltetrazol-5-ylthio)-prop-1-(t)-enyl]-ceph-3-em-4-carboxylate and 0.5 ml. of anisole at 0° C. The mixture is vigorously stirred for 30 minutes at 0° C and then evaporated to dryness under reduced pressure. The residue is mixed with ethyl ether, filtered and the trifluoroacetic acid salt of 7β-D-(α-amino-α-phenylacetamido)-4-carboxy-3-[3-(1-methyltetrazol-5-ylthio)-prop-1-(t)-enyl]-ceph-3-em collected as a white solid. This salt is then stirred with a mixture of 0.5 ml. of water and 0.5 ml. of 25%, wt., suspension of a water immiscible polymeric amine, sold under the Trademark Amberlite LA-1, by Rohm & Haas Company of Philadelphia, Pennsylvania, in methylisobutyl ketone, for one hour; the resulting solid is collected by filtration, then washed with 1:1 vol. water:-methyl isobutyl ketone, then methyl isobutyl ketone, then ethyl acetate, and then dried under vacuum affording 45 mg. of 7β-D-(α-amino-α-phenylacetamido)-3-[3-(1-methyltetrazol-5-ylthio)-prop-1-(t)-enyl]-ceph-3-em-4-carboxylic acid as an off-white powder; m.p. 155° (decomposition); uv (H₂O) 296 nm (ε 18,700); ir(KBr) 1770, 1690, 1600 cm⁻¹; nmr (CF₃CO₂D): 3.6bs, 2H (2-CH₂); 4.13s, 3H (N-Me); 4.2d, J 7 Hz, 2H (3'-CH₂); 5.23d, J 5 Hz, 1H (H-6); 5.53m, 1H (CHNH₂); 5.82dd, J 5, 8 Hz, 1H (H-7); 6.32dt, J 16, 7 Hz, 1H (H-2'); 7.4d, J 16 Hz, 1H (H-1'); 7.4-7.8m, 5H (aromatic H).

Similarly, by following the same procedure but respectively using the corresponding products of Example 5B as starting materials, the following compounds are respectively prepared:

7β-D-(α-amino-α-phenylacetamido)-3-[3-(1,2,4-triazol-5-ylthio)-prop-1-(t)-enyl]-ceph-3-em-4-carboxylic acid;

7β-D-(α-amino-α-(p-hydroxyphenyl)-acetamido)-3-[3-(1-methyltetrazol-5-ylthio)-prop-1-(t)-enyl]-ceph-3-em-4-carboxylic acid; and 7β-D-(α-amino-α-(p-hydroxyphenyl)-acetamido)-3-[3-(1,2,4-triazol-5-ylthio)-prop-1-(t)-enyl]-ceph-3-em-4-carboxylic acid.

EXAMPLE 7

This example illustrates step 7 of the process of the invention. In this example, 2.5 ml. of trifluoroacetic acid is added to a stirring mixture of 100 mg. of diphenylmethyl 7β-amino-3-[3-(1-methyltetrazol-5-ylthio)-prop-1-(t)-enyl]-ceph-3-em-4-carboxylate and 0.5 ml. of anisole at 0° C. After 3 minutes, the mixture is evaporated to dryness and the resulting residue mixed with ethyl ether affording the crystalline trifluoroacetic acid salt of 7β-amino-3-[3-(1-methyltetrazol-5-ylthio)-prop-1-(t)-enyl]-ceph-3-em-4-carboxylic acid which is then collected by filtration. The collected salt is mixed with 0.6 ml. water and 0.6 ml. of a 25% solution of a water immiscible polymeric amine (sold under the Trademark Amberlite LA-1 (acetate form) by the Rohm and Haas Company of Philadelphia, Pennsylvania) in methylisobutyl ketone and stirred for one hour at room temperature. The mixture is then filtered and the product washed three times with 2 ml. of fresh methylisobutyl ketone and twice with 5 ml. of fresh ethyl acetate and then dried under vacuum affording 45 mg. of 7β-amino-3-[3-(1-methyltetrazol-5-ylthio)-prop-1-(t)-enyl]-ceph-3-em-4-carboxylic acid as an off-white powder, m.p. 230°-235° (decomp.), ir (KBr) 1807, 1625, 1525, 1408, 1345 cm⁻¹; nmr (CF₃COOD):3.71s, 2H (2-CH₂); 4.10s, 3H (N-Me); 4.19d, J 7 Hz, 2H (3'-CH₂); 5.37m, 2H (H-6 and H-7); 6.46dt, J 7, 16 Hz, 1H (H-2'); 7.56d, J 16 Hz, 1H (H-1').

Similarly, by following the same procedure but using diphenylmethyl 7β-amino-3-[3-(1,2,4-triazol-5-ylthio)-prop-1-(t)-enyl]-ceph-3-em-4-carboxylate as the starting material, 7β-amino-3-[3-(1,2,4-triazol-5-ylthio)-prop-1-(t)-enyl]-ceph-3-em-4-carboxylic acid is prepared.

EXAMPLE 8

This example illustrates step 8 of the process of the invention. In this example, 70 μl. of dichloroacetylmandeloyl chloride is added to a stirring mixture of 0.1 g. of 7β-amino-3-[3-(1-methyltetrazol-5-ylthio)-prop-1-(t)-enyl]-ceph-3-em-4-carboxylic acid, 2 ml. of acetone and 2 ml. of 5%, wt., aqueous sodium bicarbonate solution at −20° C. The resulting mixture is stirred at −20° C for 30 minutes and allowed to come to room temperature over a period of one hour. The solution is brought to pH 9 and maintained at that pH for 30 minutes; using 5%, wt., aqueous sodium carbonate solution as required. The aqueous phase is washed with ethyl ether, then acidified (pH 2) using dilute aqueous hydrochloric acid, and extracted twice with ethyl acetate. The combined extracts are washed with brine, dried and evaporated to dryness in vacuo. The residue is mixed with a mixture of ethyl ether/hexane 1:1, by vol., and filtered and the collected solid washed again with ethyl ether/-hexane 1:1 by vol., affording 7β-(α-hydroxy-α-phenylacetamido)-3-[3-(1-methyltetrazol-5-ylthio)-prop-1-(t)-enyl]-ceph-3-em-4-carboxylic acid.

Similarly, by following the same procedure but using 7β-amino-3-[3-(1,2,3-triazol-5-ylthio)-prop-1-(t)-enyl]-ceph-3-em-4-carboxylic acid as the starting material, 7β-(α-hydroxy-α-phenylacetamido)-3-[3-(1,2,4-triazol-5-ylthio)-prop-1-(t)-enyl]-ceph-3-em-4-carboxylic acid is prepared.

EXAMPLE 8A

This example illustrates step 8 of the process of the invention. In this example, 60 μl. of phenylacetyl chloride is added to a stirring mixture of 0.1 g. 7β-amino-3-[3-(1-methyltetrazol-5-ylthio)-prop-1-(t)-enyl]-ceph-3-em- 4-carboxylic acid, 2 ml. of acetone and 2 ml. of 5%, wt., aqueous sodium bicarbonate at −10° C.

The resulting mixture is stirred at −10° C for 30 minutes and allowed to come to room temperature over a period of one hour. The mixture is then diluted with water, washed with ethyl ether, and then brought to pH 2 using dilute aqueous hydrochloric acid. The acidified mixture is extracted twice with ethyl acetate and the combined extracts washed with brine, dried and evaporated to dryness in vacuo affording a residue of crude 3-[3-(1-methyltetrazol-5-ylthio)-prop-1-(t)-enyl]-7α-phenylacetamido)-ceph-3-em-4-carboxylicc acid.

Similarly, by following the same procedure but using 7β-amino-3-[3-(1,2,4-triazol-5-ylthio)-prop-1-(t)-enyl]-ceph-3-em-4-carboxylic acid as the starting material, 3-[3-(1,2,4-triazol-5-ylthio)-prop-1-(t)-enyl]-7α-phenylacetamido-ceph-3-em-4-carboxylic acid is prepared.

EXAMPLE 8B

This example illustrates step 8 of the process of the invention. In this example, a solution of 0.1 g. of D-(−)-α-sulfophenylacetyl chloride in 3 ml. of ethyl ether is added dropwise to an ice-cold stirring mixture of 0.1 g. of 7β-amino-3-[3-(1-methyltetrazol-5-ylthio)-prop-1-(t)-enyl]-ceph-3-em-4-carboxylic acid and 5 ml. of 5%, wt., aqueous sodium bicarbonate. The mixture is stirred for one hour at 0° C. The aqueous layer is separated and washed with ethyl ether and brought to pH 1.5 by the addition of dilute aqueous hydrochloric acid and then extracted twice with ethyl acetate. The combined extracts are washed with brine, dried, and evaporated to dryness, in vacuo affording a crude residue of 3-[3-(1-methyltetrazol-5-ylthio)-prop-1-(t)-enyl]-7β-(α-phenyl-α-sulfoacetamido)-ceph-3-em-4-carboxylic acid.

Similarly, by following the same procedure but using 7β-amino-3-[3-(1,2,4-triazol-5-ylthio)-prop-1-(t)-enyl]-ceph-3-em-4-carboxylic acid as the starting material, 3-[3-(1,2,4-triazol-5-ylthio)-prop-1-(t)-enyl]-7β-(α-phenyl-α-sulfoacetamido)-ceph-3-em-4-carboxylic acid is prepared.

EXAMPLE 9

This example illustrates methods of preparing the sodium salts of the invention. In this example, 60 mg. of 7β-(α-hydroxy-α-phenylacetamido)-3-[3-(1-methyltetrazol-5-ylthio)prop-1-(t)-enyl]-ceph-3-em-4-carboxylic acid is dissolved in ethyl acetate and the sodium salt precipitated by the dropwise addition of a saturated solution of sodium 1-ethylhexanoate in ethyl acetate. The sodium salt is collected by filtration, washed twice with ethyl acetate and dried under vacuum to give the sodium salt of 7β-(α-hydroxy-α-phenylacetamido)-3-[3-(1-methyltetrazol-5-ylthio)-prop-1-(t)-enyl]-ceph-3-em-4-carboxylic acid.

Similarly, by following the same procedure, the corresponding momo, and where applicable, bis, sodium salts of the products of Examples 6B, 8A and 8B are respectively prepared.

Obviously many modifications and variations of the invention, described hereinabove and below in the claims, can be made without departing from the essence and scope thereof.

What is claimed is:
1. A compound selected from the group having the formula:

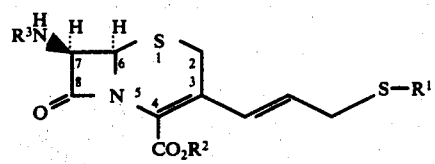

wherein the propenyl double bond is trans; $R^1$ is 1-methyltetrazol-5-yl; or 1,2,4-triazol-5-yl; $R^2$ is hydrogen, diphenylmethyl, p-methoxybenzyl, p-nitrobenzyl, o-nitrobenzyl, benzyl, t-butyl, 2,2,2,-trichloroethyl, phenacyl or pivaloyloxymethyl; $R^3$ is hydrogen or a group having the formulas:

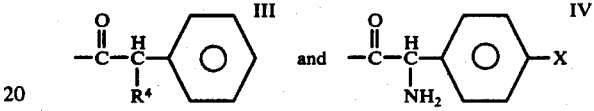

wherein $R^4$ is hydrogen, hydroxy, sulfo or carboxy; X is hydrogen or hydroxy; and pharmaceutically acceptable salts of the above compounds wherein $R^3$ is other than H.

2. The compound of claim 1 wherein the said compound is selected from the group having the formula:

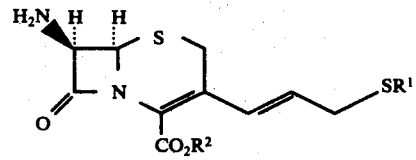

wherein $R^1$ and $R^2$ are as defined in claim 1.

3. The compound of claim 2 wherein $R^2$ is diphenylmethyl.

4. The compound of claim 3 wherein $R^2$ is hydrogen.

5. The compound of claim 4 wherein $R^1$ is 1-methyltetrazol-5-yl.

6. The compound of claim 4 wherein $R^1$ is 1,2,4-triazol-5-yl.

7. The compound of claim 1 wherein said compound is selected from the group having the formula:

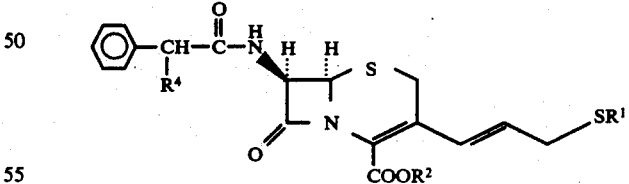

wherein $R^1$, $R^2$ and $R^4$ are as defined in claim 1, and pharmaceutically acceptable salts thereof.

8. The compound of claim 7 wherein $R^2$ is diphenylmethyl.

9. The compound of claim 7 wherein $R^2$ is hydrogen and pharmaceutically acceptable salts thereof.

10. The compound of claim 9 wherein $R^1$ is 1-methyltetrazol-5-yl.

11. The compound of claim 10 wherein said compound is a sodium salt.

12. The compound of claim 10 wherein said compound is selected from the group of 3-[3-(1-methyltetrazol-5-ylthio)-prop-1-(t)-enyl]-7β-phenylactamido-ceph-3-em-4 -carboxylic acid and pharmaceutically acceptable salts thereof.

13. The compound of claim 10 wherein said compound is selected from the group of 3-[3-(1 -methyltetrazol-5-ylthio)-prop-1-(t)-enyl]-7β-(α-hydroxy-α-phenylacetamido)-ceph-3-em-4-carboxylic acid and pharmaceutically acceptable salts thereof.

14. The compound of claim 10 wherein said compound is selected from the group of 3-[3-(1-methyltetrazol-5-ylthil)-prop-1-(t)-enyl]-7β-(α-phenyl-α-sulfoacetamido)-ceph-3-em-4-carboxylic acid and pharmaceutically acceptable salts thereof.

15. The compound of claim 10 wherein said compound is selected from the group of 3-[3-(1-methyletrazol-5-ylthil)prop-1-(t)-enyl]-7β-(α-carboxy-α-phenylacetamido)-ceph-3-em-4-carboxylic acid and pharmaceutically acceptable salts thereof.

16. The compound of claim 9 wherein R¹ is 1,2,4-triazol-5-yl.

17. The compound of claim 16 wherein said compound is a sodium salt.

18. The compound of claim 16 wherein said compound is selected from the group of 7β-phenylacetamido3-[3-(1,2,4-triazol-5-ylthio)-prop-1-(t)-enyl]-ceph-3-em-4-carboxylic acid and pharmaceutically acceptable salts thereof.

19. The compound of claim 16 wherein said compound is selected from the group of 7β-(α-hydroxy-α-phenylacetamido)-3-[3-(1,2,4-triazol-5-ylthio)-prop-1-(t)-enyl]-ceph-3-em-4-carboxylic acid and pharmaceutically acceptable salts thereof.

20. The compound of claim 16 wherein said compound is selected from the group of 7β-(α-phenyl-α-sulfoacetamido)-3-[3-(1,2,4-triazol-5-ylthio)-prop-1-(t)-enyl]-ceph-3-em-4-carboxylic acid and pharmaceutically acceptable salts thereof.

21. The compound of claim 16 wherein said compound is selected from the group of 7β-(α-carboxy-α-phenylacetamido)-3-[3-(1,2,4-triazol-5-ylthio)-prop-1-(t)-enyl]-ceph-3em-4-carboxylic acid and pharmaceutically acceptable salts thereof.

22. The compound of claim 7 wherein R⁴ is hydroxy, sulfo or carboxy and is an optically active D isomer.

23. The compound of claim 1 wherein said compound is selected from the group having the formula:

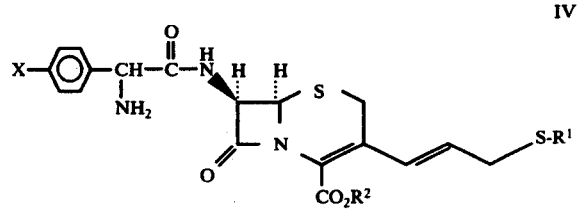

IV wherein R¹, R² and X are as defined in claim 1, and pharmaceutically acceptable salts thereof.

24. The compound of claim 23 wherein R² is diphenylmethyl.

25. The compound of claim 23 wherein R² is hydrogen and pharmaceutically acceptable salts thereof.

26. The compound of claim 25 wherein said compound is selected from the group of 3-[3-(1-methyltetrazol-5-ylthio)-prop-1-(t)-enyl]-7β-(α-amino-α-phenylacetamido)-ceph-3-em-4-carboxylic acid and pharmaceutically acceptable salts thereof.

27. The compound of claim 25 wherein said compound is selected from the group of 7β-(α-amino-α-p-hydroxyphenylacetamido)-3-[3-(1-methyltetrazol-5-ylthio)-prop-1-(t)-enyl]-ceph-3-em-4-carboxylic acid and pharmaceutically acceptable salts thereof.

28. The compound of claim 25 wherein said compound is selected from the group of 7β-(α-amino-α-phenylacetamido)-3-[3-(1,2,4-trazol-5-ylthio)-prop-1-(t)-enyl]-ceph-3-em-4-carboxylic acid and pharmaceutically acceptable salts thereof.

29. The compound of claim 25 wherein said compound is selected from the group of 7β-(α-amino-α-p-hydroxyphenylacetamido)-3-[3-(1,2,4-triazol-5-ylthio)-prop-1-(t)-enyl]-ceph-3-em-4-carboxylic acid and pharmaceutically acceptable salts thereof.

30. The compound of claim 23 wherein said compound is an optically active (D)-α-amino isomer.

31. The compound of claim 1 wherein said compound is selected from the group consisting of 7β-D-(α-hydroxy-α-phenylacetamido)-3-[3-(1methyltetrazol-5-ylthio)-prop-1-(t)-enyl]-ceph-3-em-4-carboxylic acid;

7μ-D-(α-amino-α-phenylacetamido)-3-[3-(1-methyltetrazol-5-ylthio)-prop-1-(t)-enyl]-ceph-3-em-4-carboxylic acid;

7β-D-(α-amino-α-p-hydroxyphenylacetamido)-3-[3-(1-methyltetrazol-5-ylthio)-prop-1-(t)-enyl]-ceph-3-em-4-carboxylic acid;

and pharmaceutically acceptable salts thereof.

32. A compound having the formula:

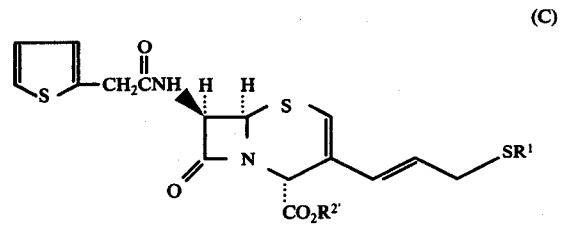

(C)

wherein the propenyl double bond is trans; R¹ is 1-methyltetrazol-5-yl or 1,2,4-triazol-5-yl; and R²'is diphenylmethyl, p-methoxy-benzyl, p-nitrobenzyl, o-nitrobenzyl, benzyl, t-butyl, 2,2,2-trichloroethyl, phenacyl or pivaloyloxymethyl.

33. A process for preparing the compounds of claim 32 which comprises reacting the corresponding 3-(1-hydroxyprop-2-enyl)-7β-(thiophen-2-yl-acetamido)-ceph-2-em-4-carboxylate ester with 5-mercapto-1-methyltetrazole or 5-mercapto-1,2,4-triazole to yield the corresponding compound of claim 41.

34. A process for preparing the compounds of claim 2 which comprises rearranging the C-2(3) double bond of the corresponding 3-[3-(1-methyltetrazol- or 1,2,4-triazol-5-ylthio)-prop-1-(t)-enyl]-7β-(thiophen-2-yl-acetamido)-ceph-2-em-4-carboxylate to the C-3(4) position via base catalysis or via oxidation and then cleaving the 7α-thiophen-2-yl-acetamido group thereby yielding the corresponding compound of claim 2.

35. A process for preparing the compounds of claim 1 of formulas III and IV, and optionally pharmaceutically acceptable salts thereof which comprises acylating the 7β-amino group and hydrolyzing the C-4-carboxylate ester of the corresponding 7β-amino-3-( 3-(1-methyltetrazol- or 1,2,4-triazol-5-ylthio)-prop-1-(t)-enyl]-ceph-3-em-4-carboxylate ester to yield the corresponding compound of formulas III and IV and optionally reacting this product with a pharmaceutically acceptable cation to obtain the corresponding salt.

36. A composition for inhibiting the growth of bacteria comprising an effective amount of a compound of claim 7 in admixture with a compatible carrier.

37. A composition for inhibiting the growth of bacteria comprising an effective amount of a compound of claim 23 in admixture with a compatible carrier.

38. A composition of claim 36 for pharmaceutical use wherein the carrier is a pharmaceutically acceptable carrier.

39. A composition of claim 37 for pharmaceutical use wherein the carrier is a pharmaceutically accceptable carrier.

* * * * *